US008009891B2

(12) United States Patent
de Vaan

(10) Patent No.: US 8,009,891 B2
(45) Date of Patent: Aug. 30, 2011

(54) SYSTEMS AND METHODS FOR IMAGE PROCESSING OF 2D MEDICAL IMAGES

(75) Inventor: Jan Anne Niels de Vaan, Houten (NL)

(73) Assignee: General Electric Company, Schenectady, NY (US)

( * ) Notice: Subject to any disclaimer, the term of this patent is extended or adjusted under 35 U.S.C. 154(b) by 1006 days.

(21) Appl. No.: 11/862,907

(22) Filed: Sep. 27, 2007

(65) Prior Publication Data
US 2009/0087053 A1    Apr. 2, 2009

(51) Int. Cl.
*G06K 9/00*     (2006.01)
*G09G 5/00*     (2006.01)
*A61B 8/00*     (2006.01)

(52) U.S. Cl. .................... 382/131; 345/629; 600/449
(58) Field of Classification Search .............. 382/131; 345/629; 600/449
See application file for complete search history.

(56) References Cited

U.S. PATENT DOCUMENTS

| | | | | |
|---|---|---|---|---|
| 5,891,030 A * | 4/1999 | Johnson et al. | ............... | 600/407 |
| 6,108,573 A * | 8/2000 | Debbins et al. | ............... | 600/410 |
| 6,898,302 B1 * | 5/2005 | Brummer | ..................... | 382/131 |
| 7,015,935 B2 * | 3/2006 | Herget et al. | ................. | 345/649 |
| 7,203,266 B2 * | 4/2007 | Fukuzawa | ......................... | 378/4 |
| 7,596,257 B2 * | 9/2009 | Kim | .............................. | 382/131 |
| 2006/0036167 A1 * | 2/2006 | Shina | ............................. | 600/433 |
| 2006/0058624 A1 * | 3/2006 | Kimura | ......................... | 600/407 |
| 2006/0122487 A1 * | 6/2006 | Tatebayashi et al. | ......... | 600/410 |
| 2007/0208248 A1 * | 9/2007 | Harvey et al. | ................. | 600/410 |
| 2007/0253610 A1 * | 11/2007 | Pieper et al. | ................. | 382/128 |
| 2008/0119723 A1 * | 5/2008 | Wegenkittl et al. | ........... | 600/416 |
| 2008/0137929 A1 * | 6/2008 | Chen et al. | ..................... | 382/131 |
| 2008/0285829 A1 * | 11/2008 | Wang et al. | ................... | 382/131 |

* cited by examiner

*Primary Examiner* — Bhavesh Mehta
*Assistant Examiner* — Utpal Shah
(74) *Attorney, Agent, or Firm* — McAndrews, Held & Malloy, Ltd.; Michael A. Dellapenna

(57) ABSTRACT

Certain embodiments of the present invention provide a system for image processing including a database, an image processor, and a display. The database includes a plurality of image slices. Each image slice in the plurality of image slices is based at least in part on an object. The image processor is adapted to generate a display image. The display image includes a selected image slice rendered about perpendicular to a localizer image. The selected image slice is selected from the plurality of image slices. The display is adapted to display the display image.

22 Claims, 5 Drawing Sheets

SYSTEMS AND METHODS FOR IMAGE PROCESSING OF 2D MEDICAL IMAGES

BACKGROUND OF THE INVENTION

The present invention generally relates to image processing. More specifically, the present invention relates to systems and methods for image processing of two-dimensional (2D) medical images.

Hospitals and other medical facilities, such as clinics and imaging centers, continually seek to improve or optimize utilization of resources and productivity. Such optimization may be achieved though faster or more understandable image processing. For example, improved image processing may include faster calculations, lower usage of computer hardware graphics, and lower storage requirements. Further, simplified images, better optimization of a single screen, and undistorted images may each improve productivity and can lead to decreased mistakes.

Many techniques are used currently to process images involving image slices. Image slices are 2D images that may be created using a tomographic scan of an object, for example. In a tomographic scan, image slices may be taken at intervals along the object. For example, each image slice may represent a single 2D axial cross-section of the object.

Image slices are not easy to interpret. From a 2D image, it is difficult to see where the image is located in the object. One common solution is to draw a cut line on a localizer image. A localizer image may be a rendition of the object that the image slices are created from. Cut lines, also known as scout-lines, are lines drawn across a localizer image. The cut line indicates where the image slice is drawn from. Typically, the localizer image and the image slice are displayed side-by-side, with the cut line on the localizer image indicating the plane in which the image slice was taken.

Although cut lines are useful, this method forces the user to divide their attention between two views. Further, there is a risk of mistakes. For example, the viewer may confuse the left-right orientation of the object. As another example, cut lines are not easy to understand by casual users, such as referring physicians and patients.

Another method of viewing image slices is full 3D image volume rendering. This method cuts down on the risk of some mistakes because the 3D visualization may be more intuitive to interpret certain aspects such as left/right. However, 3D image rendering requires 3D reconstruction which involves increased computational power and is slow to calculate. This method also may be confusing to a user due to the amount of information that is displayed. That is, a user may experience information overload. In addition, abnormalities in images are often more clearly visible in the 2D slices, and the 2D view is therefore the preferred view.

BRIEF SUMMARY OF THE INVENTION

Certain embodiments of the present invention provide a system for image processing including a database, an image processor, and a display. The database includes a plurality of image slices. Each image slice in the plurality of image slices is based at least in part on an object. The image processor is adapted to generate a display image. The display image includes a selected image slice rendered about perpendicular to a localizer image. The selected image slice is selected from the plurality of image slices. The display is adapted to display the display image.

Certain embodiments of the present invention provide a method for image processing including selecting a selected image slice from a plurality of image slices, determining a position of a localizer image with respect to the selected image slice, generating a display image, wherein the display image includes the selected image slice and the localizer image, and outputting the display image. The plurality of image slices are based at least in part on an object. The selected image slice is rendered about perpendicular to the localizer image.

Certain embodiments of the present invention provide a computer-readable medium including a set of instructions for execution on a computer, the set of instructions including an image slice selection routine, a positioning routine, an image generation routine, and a display routine. The image slice selection routine is configured to select a selected image slice from a plurality of image slices based at least in part on an object. The positioning routine is configured to determine a position of a localizer image with respect to the selected image slice. The image generation routine is configured to generate a display image. The display image includes the selected image slice and the localizer image. The selected image slice is rendered about perpendicular to the localizer image. The display routine configured to output the display image.

Figure 1:
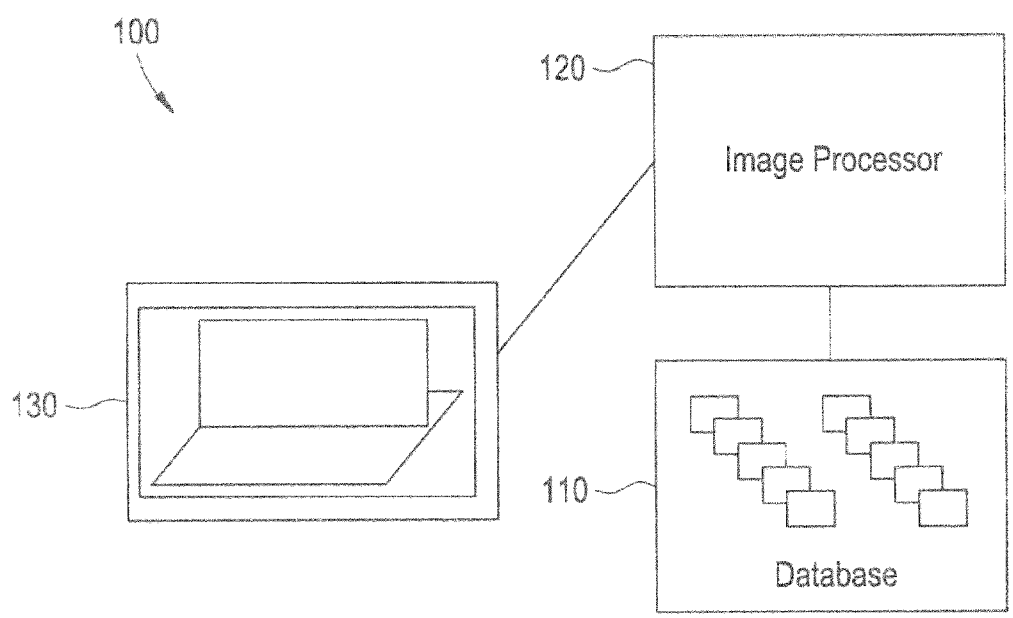
FIG. 1 illustrates a system for image processing according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a system 100 for image processing according to an embodiment of the present invention. The system 100 includes a database 110, an image processor 120, and a display 130.

The image processor 120 is in communication with the database 110 and the display 130.

In operation, the image processor 120 selects a selected image slice from the database 110. The image processor 120 generates a display image including a localizer image and the selected image slice. The display 130 displays the display image generated by the image processor 120.

The database 110 includes one or more image slices. These image slices may be taken using a scan of an object such as a patient, for example. For example, images slices may be acquired from an imaging system such as a magnetic resonance imaging (MRI), computed tomography (CT), or a Positron Emission Tomography (PET) modality.

The image processor 120 is adapted to select an image slice. The image slice may be selected from the database 110, for example. As another example, the image slice may be selected from a set of image slices received from an imaging modality.

The image processor 120 is adapted to generate a display image. For example, the image processor 120 may generate a display image including the selected image slice rendered perpendicular to a localizer image. The localizer image may be a 2D rendition of an object, for example. The localizer image may be used to show the location of the image slice in relation to the object, for example. The generated display image is discussed in more detail below. In certain embodiments, the image processor 120 utilizes a 3D rendering engine to generate the display image.

The display 130 is adapted to display a display image. The display image may be the display image that was generated by the image processor 120, for example.

In certain embodiments, the display 130 is adapted to display color images, grey-scale images, or both. In certain embodiments, the display 130 and the image processor 120 are adapted to display the display image with diagnostic quality. For example, this may be done by selecting a view angle (similar to that shown in FIG. 4B, for example) such that the axial image is undistorted by the 3D perspective. Thus, in certain embodiments, the axial image may be rendered similar to how it would be rendered by a standard 2D review workstation. This allows this presentation to be used in diagnosis without making any compromise to image quality.

The components, elements, and/or functionality of the system 100 may be implemented alone or in combination in various forms in hardware, firmware, and/or as a set of instructions in software, for example. Certain embodiments may be provided as a set of instructions residing on a computer-readable medium, such as a memory or hard disk, for execution on a general purpose computer or other processing device.

Figure 2:
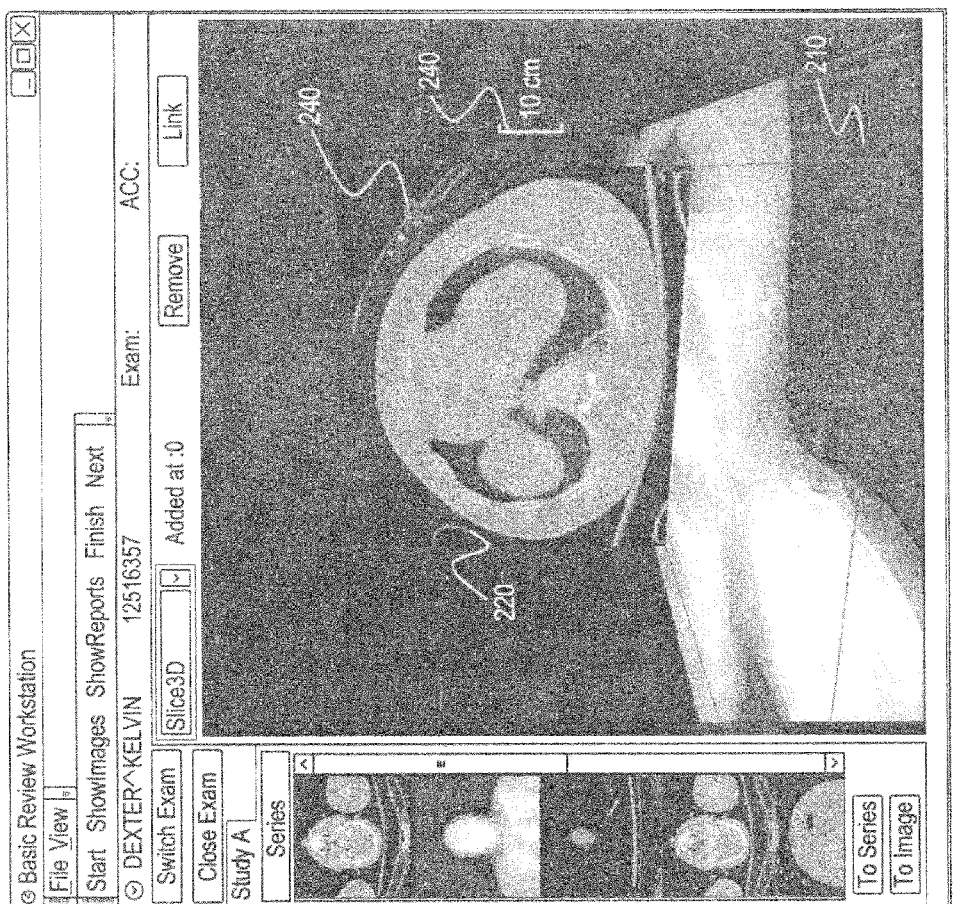
FIG. 2 illustrates a display image according to an embodiment of the present invention.

FIG. 2 illustrates a display image 200 according to an embodiment of the present invention.

As illustrated in FIG. 2, the display image 200 includes a localizer image 210, an image slice 220, and a reference tag 240. The localizer image 210 is rendered about perpendicular to the image slice 220.

In certain embodiments the localizer image 210 is based at least in part on one or more image slices in the database 110. For example, the localizer image 210 may be created from one or more image slices. The localizer image 210 may be created using one of many known 3D rendering techniques, such as Maximum Intensity Projection, Multi Planar Reformatting, or Volume Rendering.

In certain embodiments, the localizer image 210 is not created from the image slices. For example, the localizer image 210 may be an image that is representative of the object the image slices were created from. For example, the localizer image 210 may be an outline of a patient. As another example, the localizer image 210 may be a representation of a "typical" or "representative" patient of a particular gender and/or size.

In certain embodiments, the image slice 220 may intersect the localizer image 210. For example, the localizer image 210 may be rendered through the center of the image slice 220. In certain embodiments, when the image slice 220 intersects the localizer image 210, the localizer image 210 may be translucent to allow the lower portion of the image slice 220 to be visible to the user. For example, a display image may be better understood if a localizer image 210 is rendered though the center of an image slice because the user may be able to better understand and/or visualize the relationship of the localizer image 210 and the selected image slice 220.

As illustrated in FIG. 2, the image slice 220 may only intersect the localizer image 210 at an edge of the image slice 220, or intersect such that it obscures only an area of the image slice 220 where the object depicted does not extend to. Thus, the entire object shown in the image slice 220 may be visible to the user.

In certain embodiments, the image slice 220 may not intersect the localizer image 210. For example, the image slice 220 may be rendered to appear to "float above" the localizer image 210.

In certain embodiments, the angle between the localizer image 210 and the image slice 220 may be approximately ninety degrees. In certain embodiments the angle between the localizer image 210 and the image slice 220 may be predetermined, or in certain embodiments selected by a user. For example, a user may wish to view the localizer image 210 tilted at 150 degrees from the image slice 220. This may allow the user to better appreciate the localizer image, as it may be less distorted.

In certain embodiments, the image slice 220 is rendered at about the same angle with respect to the localizer image 210 as the image slice 220 was taken to the object represented by the localizer image 210.

In certain embodiments, an image slice 220 may include reference information. For example, the information may be stored within the image slice 220 or may be part of the image itself. In another example, the information may be stored with an image slice 220 in a database, associated with the image slice 220. The database may be similar to the database 110, described above, for example.

In certain embodiments, reference information may include Digital Imaging and Communications in Medicine (DICOM) attributes. DICOM is a standard for handling, storing, printing, and transmitting information in medical imaging. DICOM information may be stored in and/or with an image slice 220 so that it may be referenced by a user.

In certain embodiments, the reference information stored in and/or associated with the image slice 220 may be used to align the image slice 220 with the localizer image 210. For example, the reference information may include data concerning where (e.g., coordinates) in an object the image slice 220 was taken from. This information may be used in conjunction with information concerning the localizer image. For example, an image slice 220 may include coordinates that may be used to determine a spatial relationship to the localizer image 210. The information may describe how image pixels map on to 3D coordinates, where all the 3D coordinates for the images are defined in the same coordinate system.

In certain embodiments, reference information may be displayed to the user. That is, the display image 200 may be generated to include a reference tag 240. For example, display image 200 illustrates an embodiment of the present invention that includes a reference tag 240 within the display image 200. In certain embodiments, the display image 200 may include a reference tag 240 that shows the left/right orientation of the object that the image slice 220 is taken from. As another example, a reference tag 240 may include the location, a title for an image slice, and/or a title for an object. Further, a reference tag may show relative distance, orientation, or a degree of magnification, for example. In certain embodiments, the reference information may be taken from the image slice, DICOM information, and/or other inputted information. In certain embodiments, the reference information includes annotations on the images created by an earlier review.

In certain embodiments, the display image 200 may include more than one image slice 220. For example, a two or more image slices 220 may be selected and each may be rendered with respect to the localizer image 210 similar to the image slices described above, for example. An image slice 220 taken from a different section of an object may be rendered in a different position than a different image slice 220. Viewing more than one image slice 220 may help a user to understand the location of each particular image slice 220, for example.

In certain embodiments, an image slice 220 may be rendered translucent or transparent. For example, if two image slices 220 are selected to be rendered, the one to the forefront may be translucent. A translucent image slice 220 may allow the user to view the image slices 220 that may be behind the translucent image slice 220, for example.

In certain embodiments, one or more of the selected image slices 220 may be singled out to be shown. For example, if the display image 200 includes multiple image slices 220, one or more image slices 220 may be selected by a user to be shown. The selected image slices 220 may be rendered normally. The remaining image slices 220 in the display image 200 may be then rendered translucent, for example. The amount of translucency may be determined by a user, for example. The remaining image slices 220 may also be rendered transparent, for example. In an embodiment, the image processor 120 may only generate an outline of a non-selected image slice 220. An outline of a non-selected image slice 220 may allow a user to quickly move between image slices 220, for example. The user may be able to better understand the set of image slices 220 in this manner.

In certain embodiments, the image processor 120 is adapted to allow a user to manipulate the selected image slice using a 2D image manipulation tool. For example, the image processor 120 may allow a user to utilize a traditional 2D image tool such as a filter. As another example, a user may adjust image annotations and/or window/level.

In certain embodiments, where there may be a plurality of image slices 220 in the display image 200, the localizer image 210 may be at a fixed position in the display image 200. For example, a fixed localizer image 210 may allow different image slices 220 in the display image 200 to be selected without regenerating the entire display image 200.

Figure 3A:
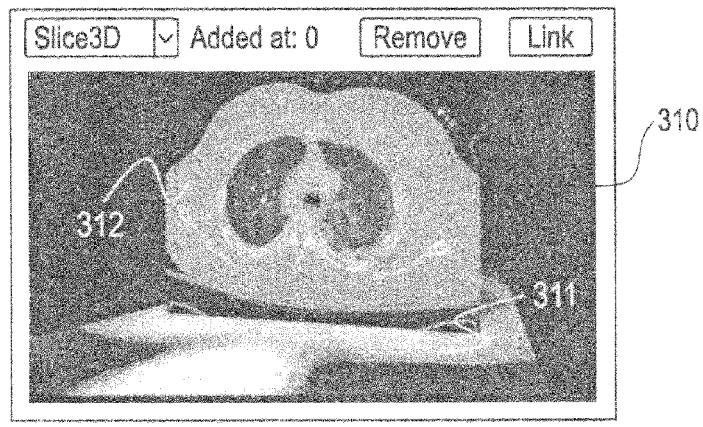
FIGS. 3A-C illustrate a sequence of three display images according to an embodiment of the present invention.
Figure 3B:
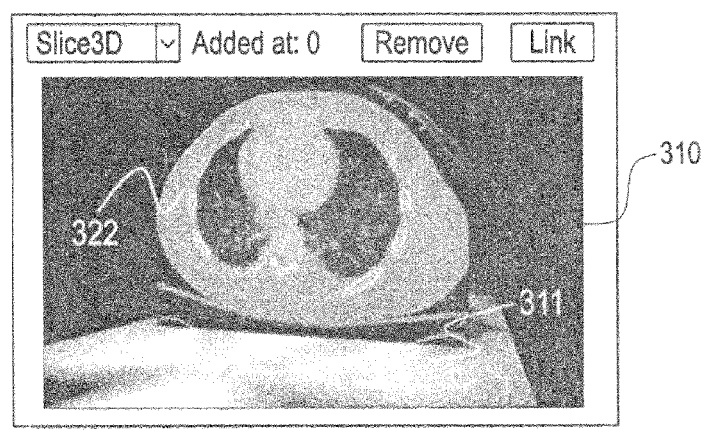
Figure 3C:
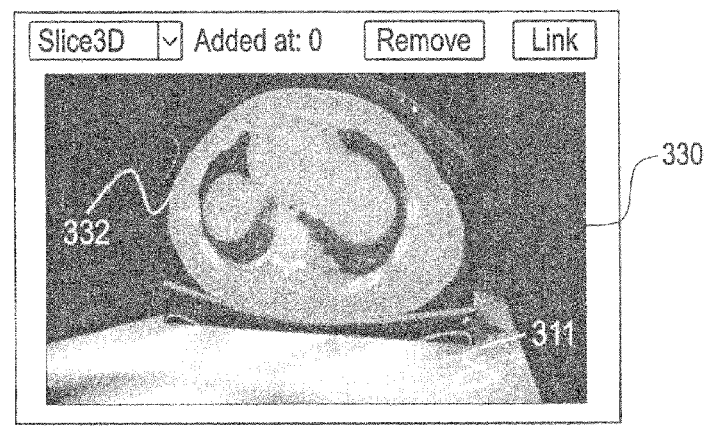

FIGS. 3A-C illustrate a sequence of three display images 310,320,330 according to an embodiment of the present invention. More particularly, FIGS. 3A-C illustrate a procession of display images 310,320,330 where a user is scrolling though more than one image slice. Display image 310 includes a localizer image 311 and an image slice 312. Display image 320 includes the localizer image 311 and an image slice 322. Display image 330 includes the localizer image 311 and an image slice 332.

As illustrated in FIGS. 3A-C, a user may scroll though image slices 312, 322, and 332. As different image slices are selected, a new display image is generated. Note that image slice 312 is closer to the head of the patient, as shown in the localizer image 311 illustrated in display image 310. Image slices 322 and 332 are progressively further from the head.

In certain embodiments, the location of the selected image slice may be fixed within the display image. That is, the localizer image 311 moves in the display image to maintain its relationship to the selected image slice. A fixed image slice may give a user a better understanding of the display image, as the size and distortion of the image slice will be maintained, for example. Interacting with a view in this configuration may be most familiar to the user, as it is similar to how some 2D image review applications work. Also, when scrolling through the slices, the user will get a rough idea of the intra-image spacing, which may be an important cue to understand the level of detail available in this direction.

In certain embodiments, the localizer image 311 is fixed while the location of the selected image slice moves to maintain its relationship to the localizer image 311.

Figure 4A:
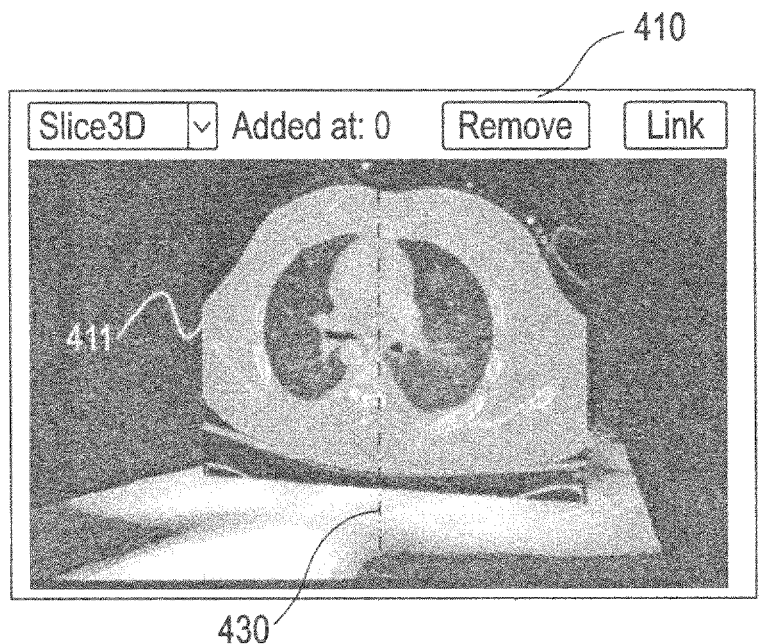
FIGS. 4A-B illustrate two display images showing the rotation of an image slice according to an embodiment of the present invention.
Figure 4B:
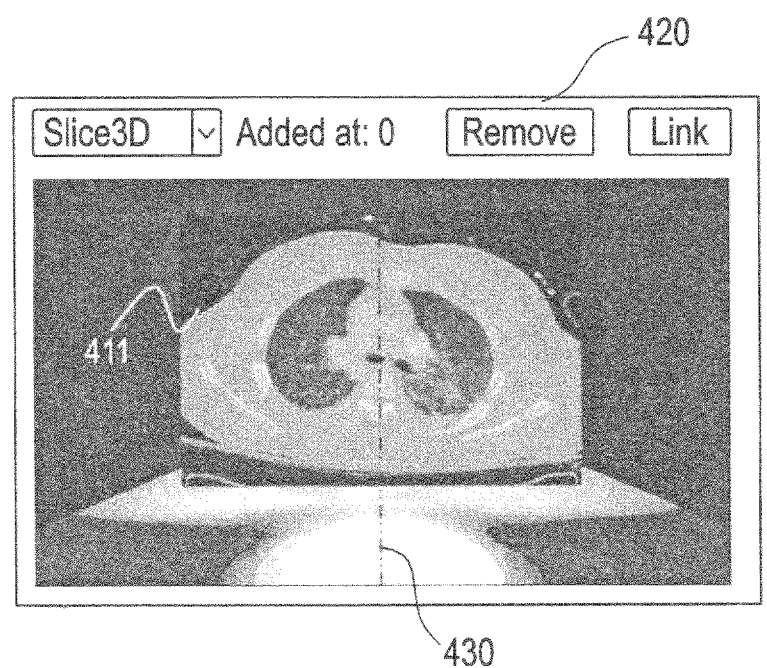

FIGS. 4A-B illustrate two display images 410,420 showing the rotation of an image slice 411 according to an embodiment of the present invention. More particularly, FIGS. 4A-B illustrate the image slice 411 in display image 410 rotated around a vertical axis 430 resulting in the display image 420.

In certain embodiments, the angle of rotation may be selected by a user. For example, a user may select to view the image slice 411 at 15 degrees off-center. As another example, the image slice 411 may be rotated 180 degrees around a vertical axis so a user is looking at the "back" of the image slice 411. Thus, for example, the head and foot of the localizer image would be reversed.

Figure 5:
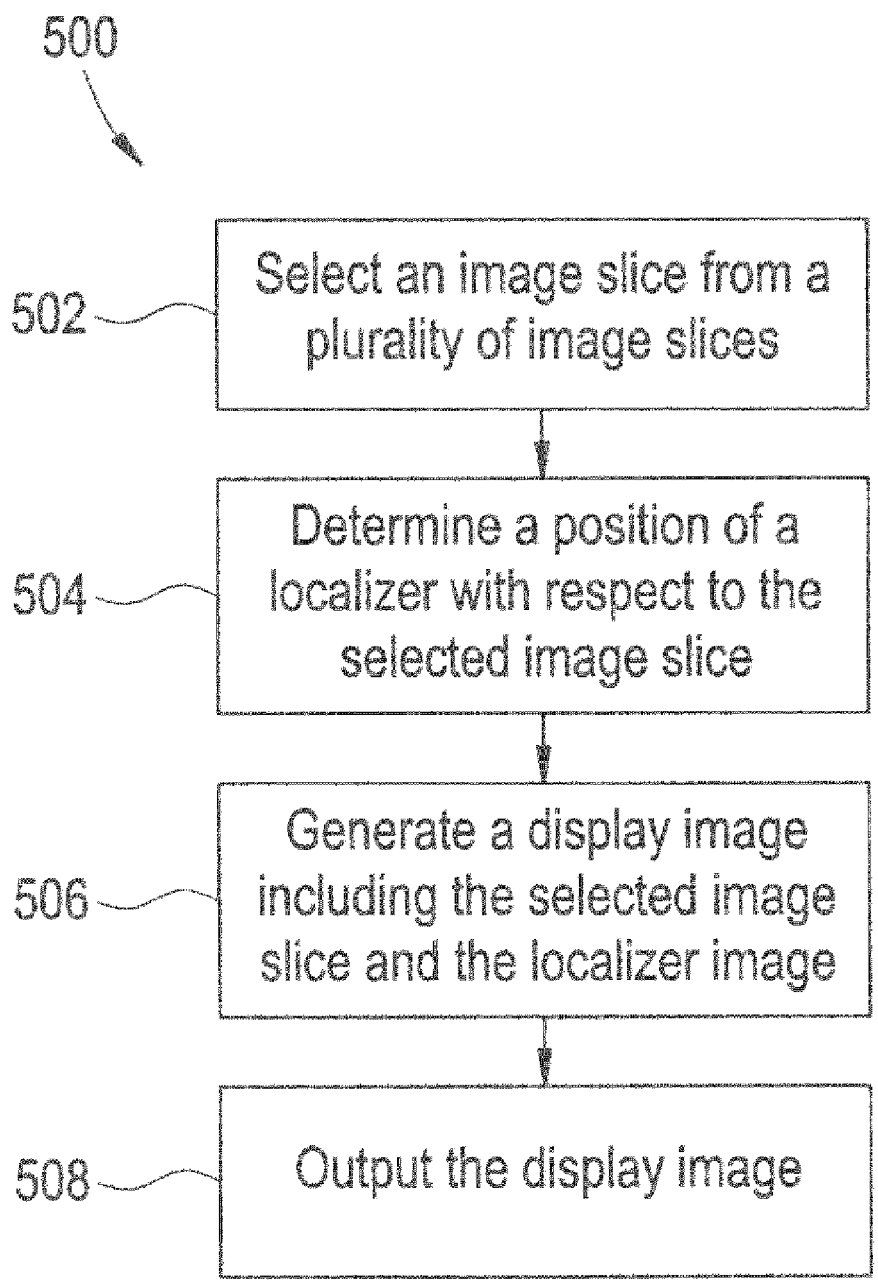
FIG. 5 illustrates a flowchart for a method of image processing according to an embodiment of the present invention.

FIG. 5 illustrates a flowchart for a method 500 of image processing according to an embodiment of the present invention. The method 500 includes the following steps, which will be described below in more detail. At step 502, an image slice is selected from a plurality of image slices. At step 504, a position of a localizer image is determined with respect to the selected image slice. At step 506, a display image including the image slice and the localizer image is generated. At step 508, the display image is outputted.

At step 502, an image slice is selected from a plurality of image slices. The plurality of image slices may be stored in a database, for example. The database may be similar to the database 110, described above, for example. The image slices may be similar to the image slices 220, 312, 322, 332, and/or 411, described above, for example. The image slice may be selected by an image processor similar to the image processor 120, described above, for example.

In certain embodiments, an image slice may be created from an object. The image slice may be taken using a scan of an object such as a patient, for example. For example, images slices may be acquired from an imaging system such as an MRI or CT modality.

In certain embodiments, an image slice may include reference information. For example, the information may be stored within the image slice 220 or may be part of the image itself. In another example, the information may be stored with an image slice 220 in a database, associated with the image slice 220. The database may be similar to the database 110, described above, for example.

In certain embodiments, reference information may include DICOM attributes. DICOM information may be stored in and/or with an image slice 220 so that it may be referenced by a user.

In certain embodiments, more than one image slice is selected.

At step 504, a position of a localizer image is determined with respect to the selected image slice. The selected image slice may be the image slice selected at step 502, described above, for example. The localizer image may be similar to the localizer image 210 and/or 311, described above, for example. The localizer image may be a 2D rendition of an object, for example. In certain embodiments, the localizer may be based at least in part on more than one image slice. The position may be determined by an image processor similar to the image processor 120, described above, for example.

In certain embodiments, the reference information stored in and/or associated with the image slice may be used to align the image slice with the localizer image. For example, the reference information may include data concerning where (e.g., coordinates) in an object the image slice was taken from. This information may be used in conjunction with information concerning the localizer image. For example, an image slice may include coordinates that may be used to determine a spatial relationship to the localizer image. The information may describe how image pixels map on to 3D coordinates, where all the 3D coordinates for the images are defined in the same coordinate system.

At step 506, a display image including the selected image slice and the localizer image is generated. The selected image slice may be the image slice selected at step 502, described above, for example. The display image may be generated based at least in part on the position determined at step 504, described above, for example. The display image may be generated by an image processor similar to the image processor 120, described above, for example. In certain embodiments, the display image may be generated using a 3D rendering engine.

In certain embodiments, the image slice may intersect the localizer image. For example, the localizer image may be rendered through the center of the image slice. In certain embodiments, when the image slice intersects the localizer image, the localizer image may be translucent to allow the lower portion of the image slice to be visible to the user. For example, a display image may be better understood if a localizer image is rendered though the center of an image slice because the user may be able to better understand and/or visualize the relationship of the localizer image and the selected image slice.

In certain embodiments, the image slice may only intersect the localizer image at an edge of the image slice. Thus, the entire image slice may be visible to the user.

In certain embodiments, the image slice may not intersect the localizer image. For example, the image slice may be rendered to appear to "float above" the localizer image.

In certain embodiments, the angle between the localizer image and the image slice may be approximately ninety degrees. In certain embodiments the angle between the localizer image and the image slice may be predetermined, or in certain embodiments selected by a user. For example, a user may wish to view the localizer image tilted at 150 degrees from the image slice. This may allow the user to better appreciate the localizer image, as it may be less distorted.

In certain embodiments, the image slice is rendered at about the same angle with respect to the localizer image as the image slice was taken to the object represented by the localizer image.

In certain embodiments, a display image including a reference tag may be generated. For example, a reference tag may be information related to the image slice, information related to the localizer image, or information relating to the display image. In certain embodiments, more than one reference tag may be generated. In certain embodiments, the reference tag includes annotations on the images created by an earlier review.

In certain embodiments, the display image may be generated with a plurality of image slices. In certain embodiments, one or more image slices may be rendered translucent. For example, if the display image includes two image slices, one may be rendered translucent so that the user is able to view the other image slice.

In certain embodiments, a sequence of display images may be generated where the localizer image appears to "move" while the selected image slice appears "fixed." This may occur when a user is scrolling through a series of image slices, for example. In certain embodiments, a sequence of display images may be generated where the localizer image appears "fixed" while the selected image slice appears to "move." This may occur when a user is scrolling through a series of image slices, for example.

In certain embodiments, the display image may be generated rotated around an axis. In certain embodiments, the angle of rotation is determined by the user. For example, the display image may be generated so that the image slice and the localizer image are off-center by 30 degrees.

At step 508, the display image is outputted. The display image may be the display image generated at step 506, discussed above, for example. The display image may be outputted by a display similar to the display 130, discussed above, for example.

In certain embodiments, the display image may be outputted with diagnostic quality. For example, the display image may be outputted undistorted by 3D perspective.

The above steps of the method 500 may be repeated. For example, a different image slice may be selected. In such a case, in certain embodiments, there may be a fixed position for the image slice in the generated display image. For example, the newly selected image slice may be in the same position as a former image slice. In certain embodiments, the position of the localizer image is fixed.

One or more of the steps of the method 500 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Thus, certain embodiments of the present invention provide systems and methods for image processing of 2D images. Certain embodiments present a 2D image slice about perpendicular to a 2D localizer image. Certain embodiments provide a technical effect of image processing of 2D images. Certain embodiments provide a technical effect of a 2D image slice about perpendicular to a 2D localizer image.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for image processing including:
   a database including a plurality of image slices, wherein each image slice in the plurality of image slices is based at least in part on an object;
   an image processor adapted to generate a display image, wherein the display image includes a selected image slice rendered about perpendicular to a localizer image, wherein the selected image slice is selected from the plurality of image slices; and
   a display adapted to display the display image.

2. The system of claim 1, wherein the display image is displayed with diagnostic quality without 3D perspective deformation.

3. The system of claim 1, wherein the display image includes a reference tag.

4. The system of claim 1, wherein the image processor is adapted to scroll though a plurality of selected image slices.

5. The system of claim 4, wherein when scrolling though more than one image slice, the selected image slice is fixed in relation to the position of an image slice in a previous display image, wherein the localizer image moves.

6. The system of claim 4, wherein when scrolling through more than one image slice, the localizer image is fixed in relation to the position of the localizer image in a previous display image, wherein the selected image slice moves.

7. The system of claim 1, wherein the localizer image is based at least in part on the plurality of image slices.

8. The system of claim 1, wherein data associated with the selected image slice is used to position the selected image slice with respect to the localizer image.

9. The system of claim 1, wherein the display image includes a plurality of selected image slices.

10. The system of claim 1, wherein the selected image slice may be rendered translucent.

11. The system of claim 1, wherein the localizer image is translucent.

12. The system of claim 1, wherein the display image is rotated around an axis.

13. The system of claim 1, wherein the display image is generated using a 3D rendering engine.

14. The system of claim 1, wherein the image processor is adapted to allow a user to manipulate the selected image slice using a 2D image manipulation tool.

15. A method for image processing including:
  selecting a selected image slice from a plurality of image slices, wherein the plurality of image slices are based at least in part on an object;
  determining a position of a localizer image with respect to the selected image slice;
  generating a display image, wherein the display image includes the selected image slice and the localizer image, wherein the selected image slice is rendered about perpendicular to the localizer image; and
  outputting the display image.

16. The method of claim 15, further including generating a second display image, wherein the second display image includes a second selected image slice and the localizer image, wherein the second selected image slice is rendered about perpendicular to the localizer image, and wherein the sequential output of the display image and the second display image results in the appearance of scrolling through the selected image slice and the second selected image slice.

17. The method of claim 16, wherein when scrolling, the position of the second selected image slice is fixed in relation to the position of the selected image slice in a previous display image, wherein the localizer image moves.

18. The method of claim 16, wherein when scrolling, the localizer image is fixed in relation to the position of the localizer image in a previous display image, wherein the selected image slice moves.

19. The method of claim 15, wherein data associated with the selected image slice is used to position the selected image slice with respect to the localizer image.

20. The method of claim 15, wherein a plurality of selected image slices is selected, wherein the display image is generated with the plurality of selected image slices.

21. The method of claim 20, further including generating the display image with one or more of the plurality of selected image slices rendered translucent.

22. A non-transitory computer-readable medium including a set of instructions for execution on a computer, the set of instructions including:
  an image slice selection routine configured to select a selected image slice from a plurality of image slices based at least in part on an object;
  a positioning routine configured to determine a position of a localizer image with respect to the selected image slice;
  an image generation routine configured to generate a display image, wherein the display image includes the selected image slice and the localizer image, wherein the selected image slice is rendered about perpendicular to the localizer image; and
  a display routine configured to output the display image.

* * * * *